(12) United States Patent
Garrison

(10) Patent No.: US 11,020,172 B2
(45) Date of Patent: Jun. 1, 2021

(54) APPARATUS FOR PERFORMING AN ELECTROSURGICAL PROCEDURE

(71) Applicant: COVIDIEN LP, Mansfield, MA (US)

(72) Inventor: David M. Garrison, Longmont, CO (US)

(73) Assignee: Covidien LP, Mansfield, MA (US)

( * ) Notice: Subject to any disclaimer, the term of this patent is extended or adjusted under 35 U.S.C. 154(b) by 298 days.

(21) Appl. No.: 16/141,204

(22) Filed: Sep. 25, 2018

(65) Prior Publication Data
US 2019/0021787 A1 Jan. 24, 2019

Related U.S. Application Data

(62) Division of application No. 14/887,529, filed on Oct. 20, 2015, now Pat. No. 10,085,795, which is a division of application No. 13/113,231, filed on May 23, 2011, now Pat. No. 9,161,807.

(51) Int. Cl.
*A61B 17/29* (2006.01)
*A61B 18/14* (2006.01)
*A61B 18/00* (2006.01)

(52) U.S. Cl.
CPC .......... *A61B 18/1447* (2013.01); *A61B 17/29* (2013.01); *A61B 17/2909* (2013.01); *A61B 2017/2925* (2013.01); *A61B 2017/2936* (2013.01); *A61B 2017/2941* (2013.01); *A61B 2018/00982* (2013.01)

(58) Field of Classification Search
CPC . A61B 17/29; A61B 17/2909; A61B 18/1447; A61B 2017/2925; A61B 2017/2936; A61B 2017/2941; A61B 2018/00982
See application file for complete search history.

(56) References Cited

U.S. PATENT DOCUMENTS

| D249,549 | S | 9/1978 | Pike |
| D263,020 | S | 2/1982 | Rau, III |
| D295,893 | S | 5/1988 | Sharkany et al. |

(Continued)

FOREIGN PATENT DOCUMENTS

| CA | 2702419 A1 | 11/2010 |
| CN | 201299462 Y | 9/2009 |

(Continued)

OTHER PUBLICATIONS

Int'l Search Report EP 08 016539.2 dated Jan. 8, 2009.

(Continued)

*Primary Examiner* — Michael F Peffley
(74) *Attorney, Agent, or Firm* — Carter, DeLuca & Farrell LLP

(57) ABSTRACT

An endoscopic forceps is provided and includes a housing having a shaft that extends therefrom. An end effector assembly is operatively connected to a distal end of the shaft and includes a pair of pivotably coupled first and second jaw members. The jaw members are movable relative to one another. A drive mechanism includes a driving structure. A link assembly includes two or more links that are operably coupled to each other and the drive structure. The two or more links are operably coupled to respective ones of the first and second jaw members.

15 Claims, 6 Drawing Sheets

(56) References Cited

U.S. PATENT DOCUMENTS

| | | |
|---|---|---|
| D295,894 S | 5/1988 | Sharkany et al. |
| 4,760,848 A * | 8/1988 | Hasson ............... A61B 17/062 |
| | | 294/115 |
| D298,353 S | 11/1988 | Manno |
| D299,413 S | 1/1989 | DeCarolis |
| D343,453 S | 1/1994 | Noda |
| 5,312,417 A | 5/1994 | Wilk |
| D348,930 S | 7/1994 | Olson |
| D349,341 S | 8/1994 | Lichtman et al. |
| D354,564 S | 1/1995 | Medema |
| 5,391,156 A | 2/1995 | Hildwein et al. |
| 5,396,900 A | 3/1995 | Slater et al. |
| D358,887 S | 5/1995 | Feinberg |
| 5,507,773 A * | 4/1996 | Huitema .......... A61B 17/07207 |
| | | 600/564 |
| 5,578,052 A | 11/1996 | Koros et al. |
| D384,413 S | 9/1997 | Zlock et al. |
| H1745 H | 8/1998 | Paraschac |
| D402,028 S | 12/1998 | Grimm et al. |
| 5,853,412 A | 12/1998 | Mayenberger |
| D408,018 S | 4/1999 | McNaughton |
| 5,904,703 A | 5/1999 | Gilson |
| 5,906,577 A | 5/1999 | Beane et al. |
| D416,089 S | 11/1999 | Barton et al. |
| 6,048,309 A | 4/2000 | Flom et al. |
| D424,694 S | 5/2000 | Tetzlaff et al. |
| D425,201 S | 5/2000 | Tetzlaff et al. |
| 6,102,909 A | 8/2000 | Chen et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,562,022 B2 | 5/2003 | Hoste et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,929,637 B2 | 8/2005 | Gonzalez et al. |
| D509,297 S | 9/2005 | Wells |
| 7,011,645 B2 | 3/2006 | McGuckin, Jr. et al. |
| 7,052,454 B2 | 5/2006 | Taylor |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,300,399 B2 | 11/2007 | Bonadio et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,473,221 B2 | 1/2009 | Ewers et al. |
| 7,559,893 B2 | 7/2009 | Bonadio et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,758,500 B2 | 7/2010 | Boyd et al. |
| D621,503 S | 8/2010 | Otten et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 8,157,786 B2 | 4/2012 | Miller et al. |
| 8,187,177 B2 | 5/2012 | Kahle et al. |
| 8,187,178 B2 | 5/2012 | Bonadio et al. |
| 8,491,624 B2 * | 7/2013 | Kerr ....................... A61B 17/29 |
| | | 606/205 |
| 8,568,443 B1 | 10/2013 | Jackman et al. |
| 8,709,035 B2 | 4/2014 | Johnson et al. |
| 8,858,588 B2 | 10/2014 | Sigmon, Jr. et al. |
| 8,998,948 B2 | 4/2015 | Hyodo |
| 9,161,807 B2 | 10/2015 | Garrison |
| 9,554,819 B2 | 1/2017 | Suzuki et al. |
| 2002/0198540 A1 | 12/2002 | Smith et al. |
| 2003/0014076 A1 | 1/2003 | Mollenauer et al. |
| 2003/0093104 A1 | 5/2003 | Bonner et al. |
| 2005/0090817 A1 * | 4/2005 | Phan .................. A61B 18/1445 |
| | | 606/41 |
| 2005/0165429 A1 | 7/2005 | Douglas et al. |
| 2006/0149306 A1 | 7/2006 | Hart et al. |
| 2006/0161049 A1 | 7/2006 | Beane et al. |
| 2006/0247500 A1 | 11/2006 | Voegele et al. |
| 2006/0247516 A1 | 11/2006 | Hess et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0073185 A1 | 3/2007 | Nakao |
| 2007/0142834 A1 * | 6/2007 | Dumbauld ......... A61B 18/1442 |
| | | 606/51 |
| 2008/0097332 A1 | 4/2008 | Greenhalgh et al. |
| 2010/0063452 A1 | 3/2010 | Edelman et al. |
| 2010/0063526 A1 | 3/2010 | Beaupre et al. |
| 2010/0198218 A1 | 8/2010 | Manzo |
| 2010/0280326 A1 | 11/2010 | Hess et al. |
| 2010/0298638 A1 | 11/2010 | Slater |
| 2010/0298646 A1 | 11/2010 | Stellon et al. |
| 2010/0298853 A1 | 11/2010 | Slater |
| 2011/0054260 A1 | 3/2011 | Albrecht et al. |
| 2011/0301637 A1 | 12/2011 | Kerr et al. |
| 2013/0030462 A1 * | 1/2013 | Keating ................ A61B 17/29 |
| | | 606/206 |
| 2013/0238017 A1 | 9/2013 | Kerr et al. |
| 2014/0074092 A1 | 3/2014 | Horner et al. |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 A1 | 1/1986 |
| DE | 3612646 A1 | 4/1987 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| DE | 202007009165 U1 | 8/2007 |
| DE | 202007009317 U1 | 8/2007 |
| DE | 202007016233 U1 | 1/2008 |
| DE | 102004026179 B4 | 1/2009 |
| DE | 102008018406 B3 | 7/2009 |
| EP | 1159926 A2 | 3/2003 |
| EP | 1312318 A1 | 5/2003 |
| EP | 2226025 A1 | 9/2010 |
| EP | 2229900 A1 | 9/2010 |
| EP | 2253283 A1 | 11/2010 |
| JP | 61501068 | 9/1984 |
| JP | 6502328 | 3/1992 |
| JP | 55106 | 1/1993 |
| JP | H0540112 A | 2/1993 |

(56) References Cited

FOREIGN PATENT DOCUMENTS

| | | |
|---|---|---|
| JP | 6121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | 08056955 | 3/1996 |
| JP | 08252263 A | 10/1996 |
| JP | 8317934 | 12/1996 |
| JP | H0910223 A | 1/1997 |
| JP | 9122138 A | 5/1997 |
| JP | H1024051 A | 1/1998 |
| JP | 10155798 | 6/1998 |
| JP | 1147150 | 2/1999 |
| JP | 11070124 | 3/1999 |
| JP | 11169381 | 6/1999 |
| JP | 11192238 | 7/1999 |
| JP | 111244298 A | 9/1999 |
| JP | 2000102545 A | 4/2000 |
| JP | 2000342599 A | 12/2000 |
| JP | 2000350732 A | 12/2000 |
| JP | 2001008944 | 1/2001 |
| JP | 2001029356 | 2/2001 |
| JP | 2001128990 A | 5/2001 |
| JP | 2001190564 A | 7/2001 |
| JP | 2004517668 A | 6/2004 |
| JP | 2004528869 A | 9/2004 |
| SU | 401367 A1 | 10/1973 |
| WO | 0036986 A1 | 6/2000 |
| WO | 0115614 A1 | 3/2001 |
| WO | 0154604 A1 | 8/2001 |
| WO | 2004054456 | 7/2004 |
| WO | 2005110264 A2 | 4/2006 |
| WO | 2010141409 | 12/2010 |

OTHER PUBLICATIONS

Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
International Search Report PCT/US01/11224 dated Nov. 13, 2001.
Int'l Search Report PCT/US01/11340 dated Aug. 16, 2001.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 050206663 dated Feb. 27, 2006.
Int'l Search Report EP 05021197.8 dated Feb. 20, 2006.
Int'l Search Report EP 050217793 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.

(56) References Cited

OTHER PUBLICATIONS

Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:376-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
International Search Report EP 04013772 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemontoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, hr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC.
Peterson et al. "Comparison of Healing Process Following Ligation with Sutures and Bipolar Vessel Sealing" Surgical Technology International (2001).
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.

(56) References Cited

OTHER PUBLICATIONS

Int'l Search Report PCT/US09/032690 dated Jun. 16, 2009.
European Search Report 11194126.6-2310 dated May 2, 2012.
European Search Report 11250792.6-2310 dated Feb. 24, 2012.

* cited by examiner

US 11,020,172 B2

APPARATUS FOR PERFORMING AN ELECTROSURGICAL PROCEDURE

CROSS-REFERENCE TO RELATED APPLICATIONS

This application is a divisional application of U.S. patent application Ser. No. 14/887,529, filed on Oct. 20, 2015, now U.S. Pat. No. 10,085,795, which is a divisional application of U.S. patent application Ser. No. 13/113,231, filed on May 23, 2011, now U.S. Pat. No. 9,161,807, the entire contents of each of which are hereby incorporated herein by reference.

BACKGROUND

Technical Field

The present disclosure relates to an apparatus for performing an electrosurgical procedure. More particularly, the present disclosure relates to an electrosurgical apparatus including an end effector assembly having a pair of jaw members that provide a mechanical advantage at the end effector.

Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members that are configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive element, is utilized to cooperate with one or more components operatively associated with the end effector to impart movement to one or both of the jaw members.

To facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more cam members, e.g., a cam pin, may operably couple to the drive element, e.g., a drive rod, wire, cable, etc., and operably couple to a cam slot that is operably associated with one or both of the jaw members. Typically, the cam slots are operably disposed on proximal ends of the jaw members. In certain instances, the proximal ends of the jaw members are configured to extend outside of the shaft profile. In the extended position, the proximal ends of the jaw members are commonly referred to as "flags."

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) any forces or frictional losses at the distal end of the shaft including those caused by the "flags" extending through the shaft profile and having to displace the flexible insulation may be transferred to the drive rod, drive element, and/or a spring operably associated with the drive assembly, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

SUMMARY

The present disclosure provides an endoscopic forceps. The endoscopic forceps includes a housing having a shaft that extends therefrom and defines a longitudinal axis therethrough. An end effector assembly is operatively connected to a distal end of the shaft and includes a pair of first and second jaw members. The first and second jaw members are pivotably coupled to one another. The first and second jaw members are movable relative to one another from an open position, wherein the first and second jaw members are disposed in spaced relation relative to one another, to a clamping position, wherein the first and second jaw members cooperate to grasp tissue therebetween. A drive mechanism includes a driving structure. A link assembly includes two or more links that are operably coupled to each other and the driving structure. The two or more links are operably coupled to respective ones of the first and second jaw members at proximal ends thereof. The proximal ends of the first and second jaw members each includes a stop member that is configured to contact the respective one of the at least two links. The stop members of the first and second jaw members include a generally slanted trailing edge that is configured to contact a leading edge of the respective one of the at least two links as the at least two links transition past vertical such that the first and second jaw members are releasably maintained in the clamping position.

The present disclosure provides endoscopic forceps. The endoscopic forceps includes a housing having a shaft that extends therefrom and defines a longitudinal axis therethrough. The shaft has a cam operably disposed thereon adjacent a distal end thereof. An end effector assembly is operatively connected to a distal end of the shaft adjacent the cam and includes a pair of first and second jaw members pivotably coupled to one another. One or both of the first and second jaw members are movable relative to the other jaw member from an open or neutral position, wherein the first and second jaw members are disposed in spaced relation relative to one another, to a clamping position, wherein the first and second jaw members cooperate to grasp tissue therebetween. A drive mechanism includes a driving structure. A link assembly includes two or more links. A top portion of one of the links operably couples to a bottom portion of the other link. The top and bottom portions of the links are operably coupled to each other and the driving structure via a pivot pin. The two or more links are operably coupled to respective ones of the first and second jaw members at proximal ends thereof.

BRIEF DESCRIPTION OF THE DRAWING

Various embodiments of the present disclosure are described hereinbelow with references to the drawings, wherein.

DETAILED DESCRIPTION

Figure 1:
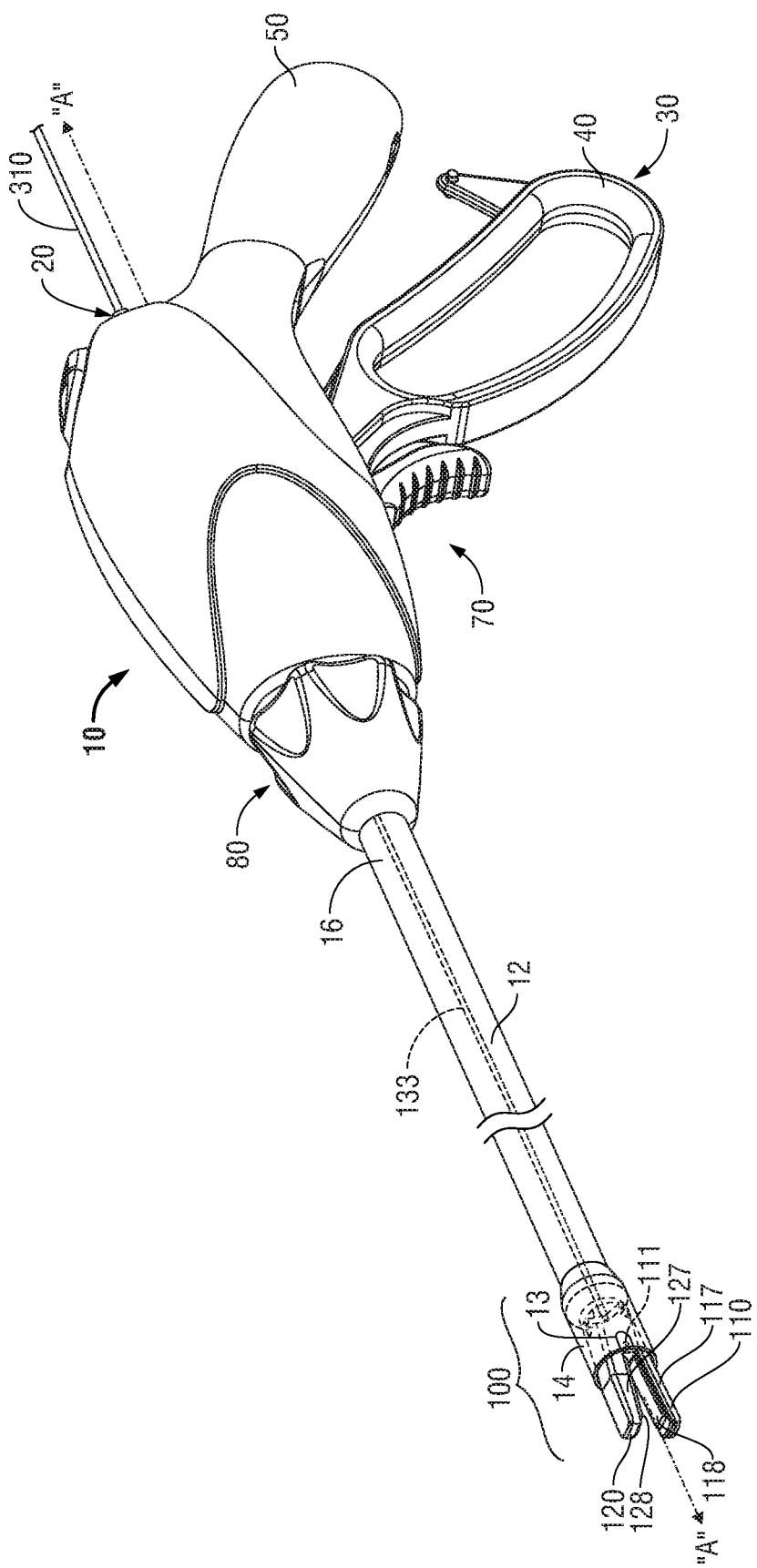
FIG. 1 is a side, perspective view of an endoscopic bipolar forceps showing an end effector assembly including jaw members according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end which is closer to the user, while the term "distal" will refer to an end that is farther from the user.

Figure 2:
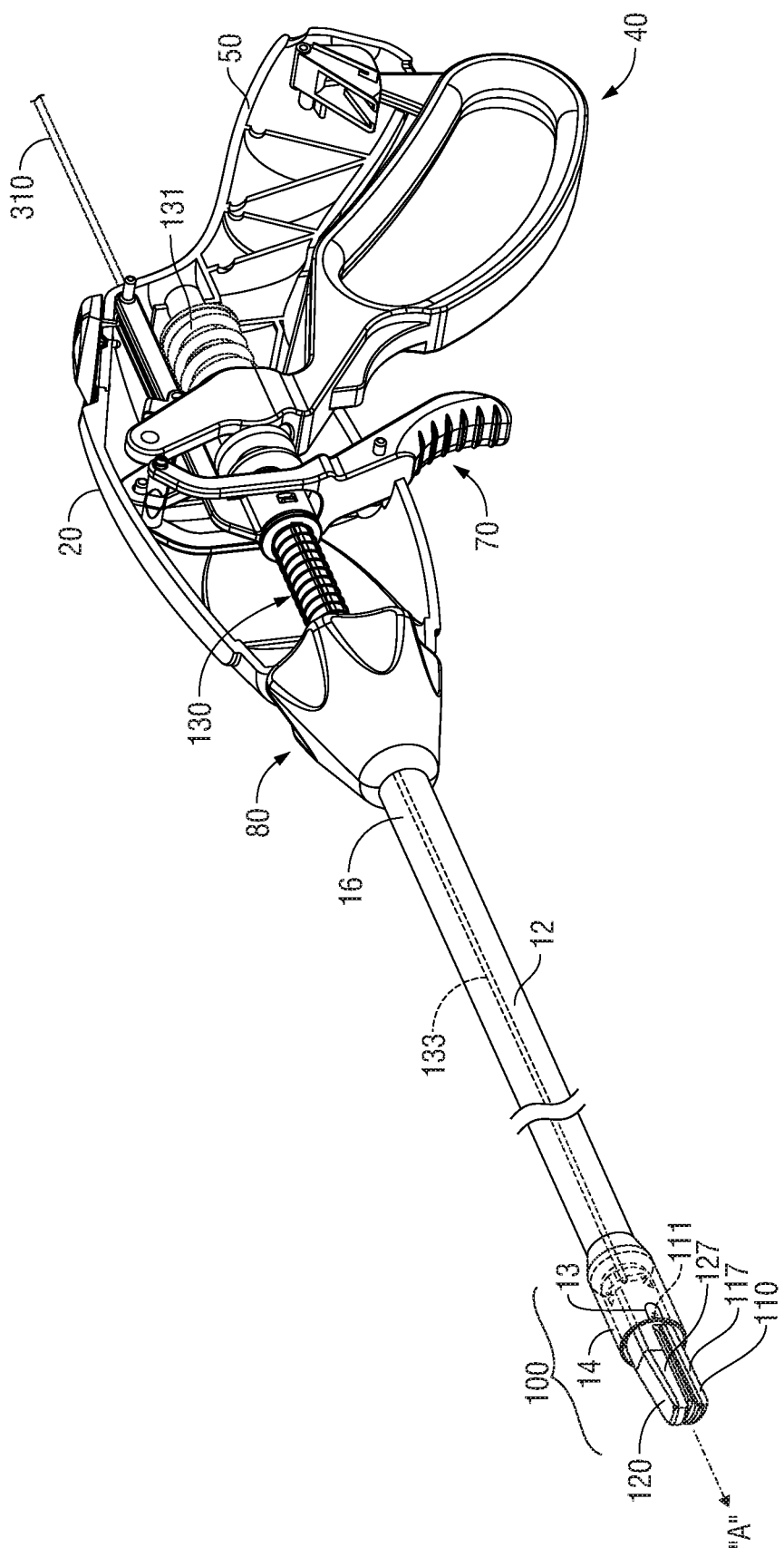
FIG. 2 is a side, perspective view of the endoscopic bipolar forceps depicted in FIG. 1 illustrating internal components associated with a handle assembly associated with the endoscopic bipolar forceps.

With reference to FIGS. 1 and 2, an illustrative embodiment of an electrosurgical apparatus, e.g., a bipolar forceps 10 (forceps 10) is shown. Forceps 10 is operatively and selectively coupled to an electrosurgical generator (not shown) for performing an electrosurgical procedure. As noted above, an electrosurgical procedure may include sealing, cutting, cauterizing coagulating, desiccating, and fulgurating tissue all of which may employ RF energy. The electrosurgical generator may be configured for monopolar and/or bipolar modes of operation and may include or be in operative communication with a system that may include one or more processors in operative communication with one or more control modules (not shown) that are executable on the processor. The control module may be configured to instruct one or more modules to transmit electrosurgical energy, which may be in the form of a wave or signal/pulse, via one or more cables (e.g., an electrosurgical cable 310) to the forceps 10.

Forceps 10 is shown configured for use with various electrosurgical procedures and generally includes a housing 20, an electrosurgical cable 310 that connects the forceps 10 to the electrosurgical generator, a rotating assembly 80 and a trigger assembly 70. For a more detailed description of the rotating assembly 80, trigger assembly 70, and electrosurgical cable 310 (including line-feed configurations and/or connections), reference is made to commonly-owned U.S. patent application Ser. No. 11/595,194 filed on Nov. 9, 2006, now U.S. Patent Publication No. 2007/0173814.

With continued reference to FIGS. 1 and 2, forceps 10 includes a shaft 12 that has a distal end 14 configured to mechanically engage an end effector assembly 100 operably associated with the forceps 10 and a proximal end 16 that mechanically engages the housing 20.

A cam slot 13 of suitable configuration is positioned at the distal end 4 of the shaft 12 and is configured to receive a pivot pin 111 therein such that the pivot pin 111 may translate therein (FIGS. 1-4). In the illustrated embodiment, the cam slot 13 is defined through the shaft 12.

Figure 3:
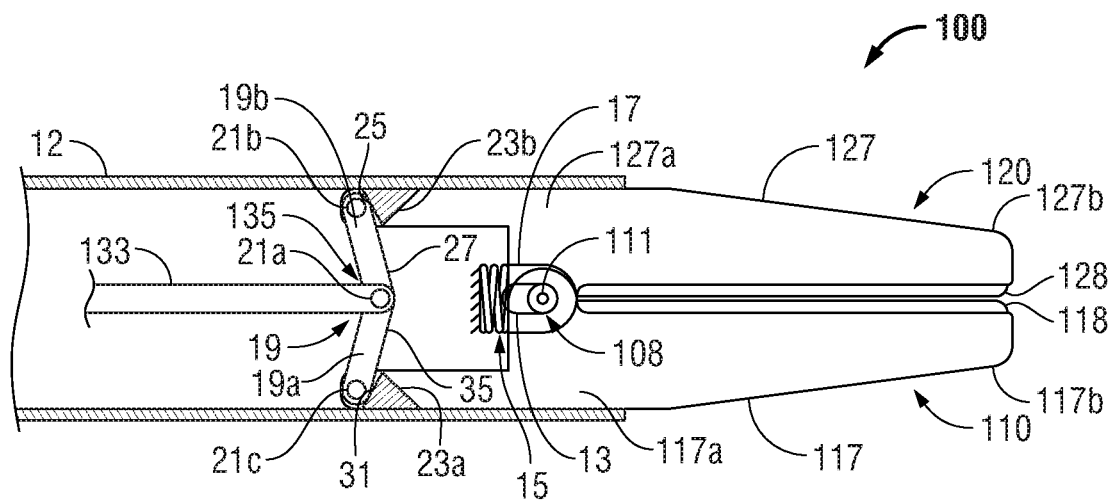
FIG. 3 is a schematic view of the jaw members depicted in FIGS. 1 and 2 illustrating a distal end of a driving structure operably coupled to the jaw members.
Figure 4:
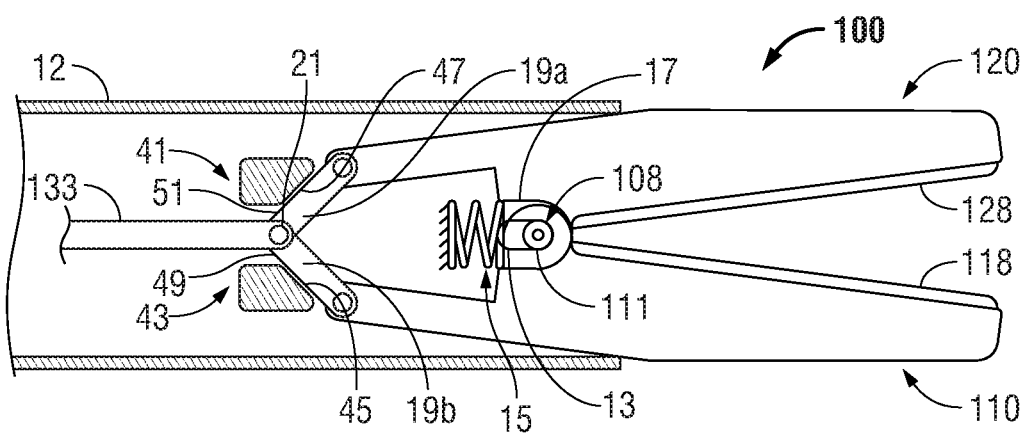
FIG. 4 is a schematic view illustrating a distal end of the driving structure depicted in FIG. 3 according to another embodiment of the present disclosure.

A resilient member in the form of a compression spring 15 is provided at the distal 14 end of the shaft 12. In particular, the spring 15 is grounded to an internal wall of the shaft 12 and couples to the pivot pin 111 via a one or more suitable coupling methods (FIGS. 3 and 4). In the illustrated embodiment, a spring coupler 17 operably couples the pivot pin 111 to the spring 15.

Handle assembly 30 includes a fixed handle 50 and movable handle 40 (FIGS. 1 and 2). In one particular embodiment, fixed handle 50 is integrally associated with housing 20. Movable handle 40 is movable relative to fixed handle 50 for effecting movement of one or more components, e.g., driving structure 133, operably associated with a drive mechanism 130 (FIGS. 2 and 3). Handle assembly 30 including movable handle 40 may be configured such that proximal movement of the movable handle 40 "pushes" the driving structure 133, which, in turn, imparts movement of the jaw members 110 and 120 from a normally open position (FIG. 1) to closed or clamping position (FIGS. 2 and 3). Alternatively, handle assembly 30 including movable handle 40 and drive mechanism 130 may be configured such that proximal movement of the movable handle 40 "pulls" the driving structure 133, which, in turn, imparts movement of the jaw members 110 and 120 from a normally an open position (FIG. 1) to a closed position, wherein the jaw members 110 and 120 are configured to grasp tissue therebetween.

Drive mechanism 130 is in operative communication with movable handle 40 (see FIGS. 1 and 2) for imparting movement of one or, in some instances, both of the jaw members 110, 120 of end effector assembly 100. More particularly, one or more suitable mechanical interfaces, e.g., a linkage interface, gear interface, or combination thereof operably couples the movable handle 40 to the drive mechanism 130. In the embodiment illustrated in FIGS. 1-3, proximal movement of the movable handle 40 moves the jaw members 110 and 120 toward each other from the normally open position to the clamping position.

Driving structure 133 is configured such that distal movement thereof causes the jaw members 110 and 120 to move from the open position (FIG. 1) to the clamping position (FIGS. 2 and 3) and vice versa. To this end, driving structure 133 may be any suitable driving structure or mechanism including but not limited to a wire, rod, cable, band, etc. In the illustrated embodiment, driving structure 133 is a substantially flexible drive rod 133 of suitable proportion that is dimensioned to translate within the shaft 12 (see FIGS. 1-3). Drive rod 133 is dimensioned such that the drive rod 133 does not to "buckle" or "kink" when the drive rod 133 is moved distally and/or proximally within the shaft 12. Drive rod 133 includes a proximal end (not explicitly shown) that is in operative communication with the movable handle 40.

With reference to FIG. 3, a distal end 135 of the drive rod 133 operably couples to the end effector 100 and/or jaw members 110 and 120. More particularly, and in the embodiment illustrated in FIG. 3, a pivot pin 21a (or rivet, fastener, living-hinge or the like) operably couples the distal end 135 of the drive rod 133 to a link assembly 19.

Link assembly 19 is an over-the-center link type and includes two or more links. In the embodiment illustrated in FIG. 3, link assembly 19 includes two links 19a and 19b. Links 19a and 19b are pivotably coupled to each other via one or more suitable coupling methods. More particularly, pivot pin 21a operably couples the distal end 135 of the drive rod 133 to a top portion of the link 19a and a bottom portion of the link 19b. Link assembly 19 including links 19a and 19b serves to latch the jaw members 110 and 120 in the closed or clamping position when the links 19a and 19b and/or pivot pin 21a moves past a center point of the link assembly 19. That is, as the links 19a and 19b transition past vertical, the links 19a and 19b are configured to contact and/or releasably engage the jaw members 110 and 120 (or component associated therewith) of the end effector such that the jaw members 110 and 120 remain in the closed or clamping position, described in greater detail below. As can be appreciated, having the link assembly 19 serve as a latch may eliminate the need for a separate latching device in the housing 20 and/or handle assembly 30 as is typically utilized with conventional forceps. Moreover, the link assembly 19 provides an additional mechanical advantage when closing the jaw members 110 and 120 at the beginning of a closing or clamping stroke (i.e., when the movable handle 40 is moved proximally). That is, due to the geometries of the links 19a and 19b, the force at the jaw members 110 and 120 is controlled by the geometry and stiffness of the links 19a and 19b and/or the jaw members 110 and 120 (or operative components associated therewith).

A top portion of the link 19b operably couples to jaw member 120. More particularly, a pivot pin 21b operably couples the top portion of the link 19b to a proximal end 127a of the jaw member 120 (FIG. 3). Likewise, a pivot pin 21c operably couples a top portion of the link 19a to the jaw member 110 (FIG. 3).

End effector assembly 100 is illustrated operably disposed at the distal end 14 of the shaft 12 (FIGS. 1-3). End effector assembly 100 includes opposing jaw members 110 and 120 that mutually cooperate to grasp, seal and, in some cases, divide large tubular vessels and large vascular tissues. As noted above, in the illustrated embodiment, jaw members 110 and 120 are movable relative to each other. Jaw members 110, 120 are operatively and pivotably coupled to each other via a pivot pin 111 and are located adjacent the distal end 14 of shaft 12. Electrically conductive seal plates 118 and 128 are operably supported on and secured to respective distal ends 117b and 127b of jaw housings 117 and 127. Jaw members 110 and 120 including respective jaw housings 117 and 127, and operative components associated therewith, may be formed from any suitable material, including but not limited to metal, metal alloys, plastic, plastic composites, ceramics, ceramic composites, and so forth.

Jaw housing 127 and 117 of the respective jaw members 110 and 120 are substantially identical to each other. In view thereof, the operative features of jaw housing 127 are described in detail, and only those features that are unique to jaw member 110 are described hereinafter.

With continued reference to FIG. 3, an embodiment of jaw housing 127 is illustrated. Jaw housing 127 includes distal end 127b that is configured to operably support seal plate 128 and proximal end 127a that operably couples to the distal end 14 of shaft 12 and to the top portion of the link 19b. Proximal end 127a includes a generally elongated configuration, and is dimensioned to move, e.g., pivot, within the shaft 12 from the open position to the closed or clamping position. Pivot pin 111 couples the first and second jaw members 110 and 120, respectively (FIG. 3) for pivotal movement relative to one another.

Proximal end 127a serves as a beam that, in concert with the links 19a and 19b, regulates a clamping force at the jaw members 110 and 120 when the links 19a and 19b transition past vertical and the jaw members 110 and 120 are in the clamping position with tissue disposed therebetween. Proximal end 127a may be relatively resilient, or in some instances, may be substantially rigid. The resiliency, or lack thereof, may be varied based on a specific surgical procedure, manufacturer and/or user preference, etc. In the embodiment illustrated in FIG. 3, proximal end 127a is relatively resilient.

One or more stop members 23b (one stop member 23b is illustrated in the drawings) are operably disposed on the proximal end 127a of the jaw housing 127. Stop member 23b is configured to contact and/or releasably engage the link 19b of the link assembly 19 when the links 19a and 19b have transitioned past vertical. More specifically, stop member 23b includes an angled trailing edge 25 that is configured to contact a leading edge 27 of the link 19b. This contact between the angled trailing edge 25 of the stop 23b and the leading edge 27 of the link 19b facilitates "latching" jaw member 120 in the clamping position. That is, when the angled trailing edge 25 contacts the leading edge 27, the links 19a and 19b including pivot pin 21a are prevented from moving distally.

Jaw housing 117 of jaw member 110 includes components similar to that of the components associated with jaw housing 127 of jaw member 120. More particularly, jaw housing 117 includes proximal end 117a that functions similarly to that of proximal end 127a of jaw housing 127a. Proximal end 117a of the jaw member 110 includes a stop member 23a having an angled trailing edge 31 that is configured to contact a corresponding leading edge 35 of the link 19a. Stop 23a functions in a manner substantially similar to that of stop 23b.

The jaw members 110 and 120 may be coupled to each other via any suitable coupling methods. In the illustrated embodiment, an opening 108 is defined in and extends through each jaw housing 117 and 127 and is configured to receive pivot pin 111. Opening 108 is shown engaged with pivot pin 111 and as such is not explicitly visible.

In an assembled configuration, pivot pin 111 is positioned within the openings associated with each of the jaw members 110 and 120. Once assembled, the jaw members 120 and/or jaw member 110 may be pivotably supported at the distal end 14 of the shaft 12 by known methods, such as, for example, by the method described in commonly-owned U.S. Pat. No. 7,597,693 to Garrison filed on Jun. 13, 2003.

In use, jaw members 110 and 120 are, initially, in the open position (FIG. 1). Tissue is positioned between the jaw members 110 and 120. Once tissue is positioned between the jaw members 110 and 120, movable handle 40 is moved proximally (FIG. 2), which, in turn, causes the drive rod 133 to move distally. Distal movement of drive rod 133 causes the links 19a and 19b to pivot, i.e., in respective clockwise and counterclockwise directions, about pivot pins 21a-21c and move distally. As links 19a and 19b move distally, the pivot pin 111 moves distally against the bias of the spring 15 and the jaw members 110 and 120 move toward one another and to the clamping position. Ultimately, links 19a and 19b transition past vertical and the respective leading edges 35 and 27 of links 19a and 19b contact respective trailing edges 31 and 25 of stops 23a and 23b. Contact between the leading edges 35 and 27 and trailing edges 31 and 25 "latches" the jaw members 110 and 120 in the clamping position. Thereafter, tissue is electrosurgically treated, e.g., tissue is sealed. Subsequently, movable handle 40 is released and pivot pin 15 moves proximally and the jaw members 110 and 120 move away from one another and back to the open or neutral position.

The unique configuration of the link assembly 19 including links 19a and 19b and proximal ends 117a and 127a improves the opening and closing angles typically associated with known forceps jaw designs. Moreover, the unique configuration of the link assembly 19 including links 19a and 19b and proximal ends 117a and 127a eliminates the need of having the proximal ends 117a and 127a ("flags") extend past the profile of the shaft 12.

With reference to FIG. 4, in certain embodiments, a cam member 41 may be operably coupled to the shaft 12 and operably disposed adjacent the end effector 100. For illustrative purposes, the stop members 23a and 23b are not shown in FIG. 4. The cam member 41 is configured to cam the links 19a and 19b toward a horizontal position and each other as the drive rod 133 is moved proximally. To this end, the cam member 41 includes an opening 43 that is configured to receive the drive rod 133 therethrough. Cam member 41 includes slanted leading edges 45 and 47 that are configured to contact respective trailing edges 49 and 51 of links 19a and 19b such that the jaw members 110 and 120 remain in the open or neutral position.

In use and with movable handle 40 in a distal position (see FIG. 1 for example), the trailing edges 49 and 51 of links 19a and 19b contact the leading edges 45 and 47 of the cam member 41. This contact between trailing edges 49, 51 and the leading edges 45, 47 force the links 19a and 19b to pivot about the pivot pin 21a and maintain the jaw members 110 and 120 in the open or neutral position.

From the foregoing and with reference to the various figure drawings, those skilled in the art will appreciate that certain modifications can also be made to the present disclosure without departing from the scope of the same. For example, it is contemplated that in certain instances one or more resilient members, e.g., a compression spring 200, may be operably associated with or coupled to either the link assembly 19 including links 19a and 19b and/or one or both of the jaw members 110 and 120 (see FIG. 5, for example). More particularly, a compression spring 200 may be coupled to the pivot pin 21a and the pivot pin 111 by one or more suitable coupling methods, e.g., soldering. In this instance, the spring 200 may be configured to provide a clamping force or seal force in the range of about 3 kg/cm$^2$ to about 16 kg/cm$^2$ between the jaw members 110 and 120 when the jaw members 110 and 120 are in the clamping position.

Figure 5:
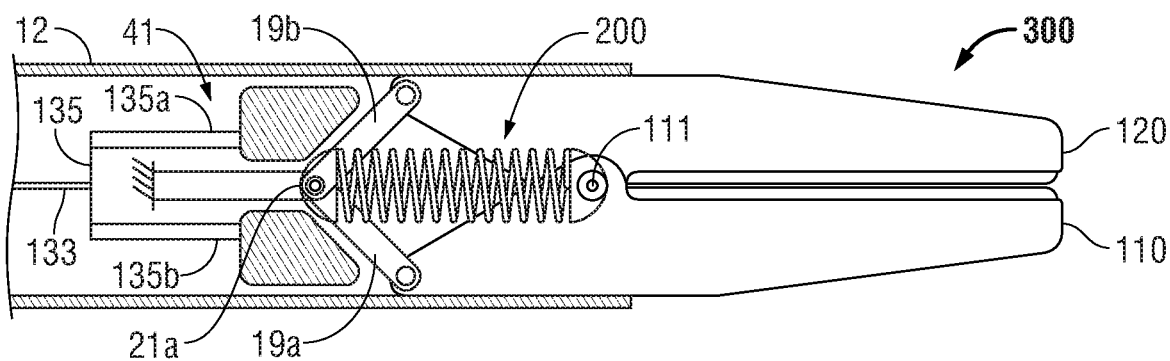
FIG. 5 is a schematic view illustrating an end effector assembly including jaw members according to another embodiment of the present disclosure.

With reference to FIG. 5, an end effector assembly 300 is illustrated. End effector assembly 300 is substantially similar to end effector 100. As a result thereof, only those features unique to end effector 300 are described herein. In the embodiment illustrated in FIG. 5, the cam member 41 is configured to translate along the longitudinal axis "A-A" (see FIG. 5). More particularly, cam member 41 is movable from a proximal position that corresponds to the jaw members 110 and 120 being in the clamping position to a distal position that corresponds to the jaw members being in the open position.

Unlike the previously described embodiments, the cam member 41 operably couples (via one or more suitable coupling methods, e.g., soldering) to a bifurcated distal end 135 having bifurcated ends 135a and 135b and the link assembly 19 is fixedly attached to an internal frame of the shaft 12. Operation of the forceps 10 with the end effector 200 is substantially similar to that of end effector 100. A distinguishing feature of the operation of the forceps 10 with the end effector 300 when compared to the end effector 100, is that the jaw members 100 and 200 are biased in the clamping configuration by the spring 200 that provides a clamping force or seal force in the range of about 3 kg/cm$^2$ to about 16 kg/cm$^2$ between the jaw members 110 and 120. Moreover, when movable handle 40 is moved proximally, cam member 41 moves distally and contacts the links 19a and 19b, which, in turn, causes the links 19a and 19b to pivot about the pivot pin 21a and the jaw members 110 and 120 to move away from each other to the open position against the bias of the spring 200.

Figure 6:
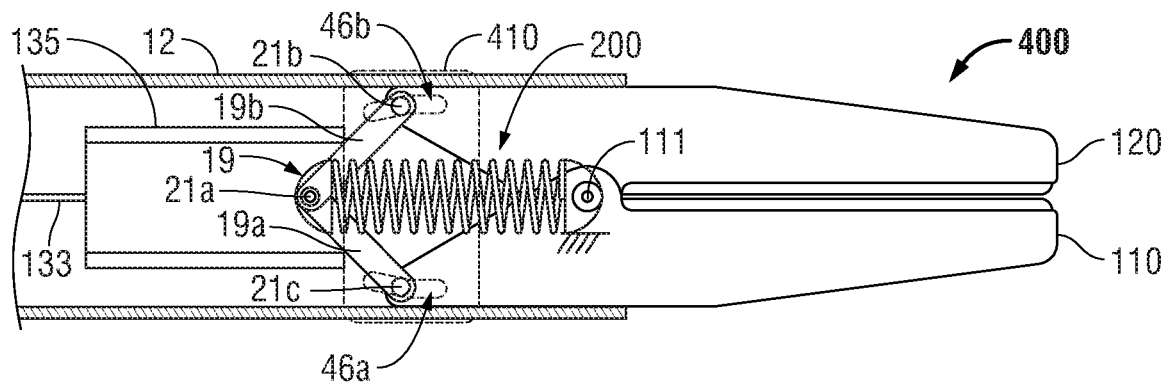
FIG. 6 is a schematic view illustrating an end effector assembly including jaw members according to yet another embodiment of the present disclosure.

With reference to FIG. 6, an end effector assembly 400 is illustrated. End effector assembly 400 is substantially similar to end effectors 100 and 300. As a result thereof, only those features unique to end effector 400 are described herein. In the embodiment illustrated in FIG. 6, a cam member 410 includes two generally arcuate slots 46a and 46b that respectively couple to pivot pins 21c and 21b of the links 19a and 19b (see FIG. 6). Operation of the forceps 10 with the end effector 400 is substantially similar to that of end effector 300. However, unlike cam member 41, distal movement of the cam member 410 causes the pivot pins 21c and 21b to translate distally within the arcuate cam slots 46a and 46b, respectively, which, in turn, causes the jaw members 110 and 120 to move away from each other to the open position against the bias of the spring 200.

Figure 7:
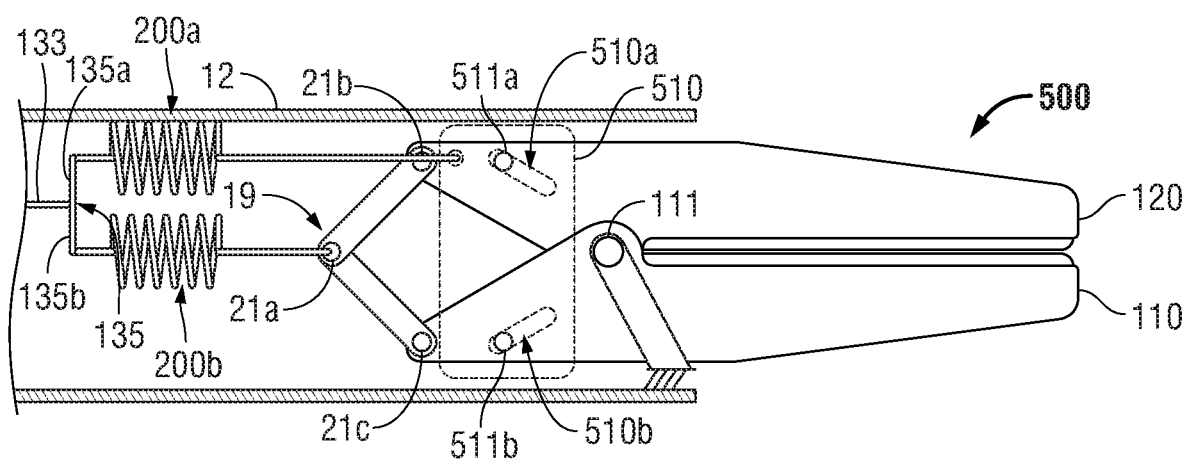
FIG. 7 is a schematic view illustrating an end effector assembly including jaw members according to still another embodiment of the present disclosure.

With reference to FIG. 7, an end effector assembly 500 is illustrated. End effector assembly 500 is substantially similar to end effectors 100 and 300. As a result thereof, only those features unique to end effector 500 are described herein.

The distal end 135 of the driving structure 133 is bifurcated or split with two legs or branches 135a and 135b that couple to respective resilient members 200a and 200b.

Resilient members 200a and 200b may be any suitable type of resilient member including but not limited to: springs selected from the group consisting of coil, leaf and tension; gas or fluid pistons; and elastomers or other compliant materials.

A proximal end of the resilient member 200a operably couples to the branch 135a of the driving structure 133 by any of the aforementioned coupling methods (e.g., soldering, welding, or solid joints) and a distal end of the resilient member 200a operably couples (e.g., also by soldering) to a movable cam member 510 (cam member 510). Likewise, a proximal end of the resilient member 200b operably couples, e.g., via soldering, to the branch 135b of the driving structure 133 and a distal end of the resilient member 200b operably couples (e.g., also by soldering) to the pivot pin 21a of the link assembly 19. To facilitate moving cam member 510, the resilient members 200a and 200b are disposed in different horizontal planes from each other. More particularly, resilient member 200a is located above the resilient member 200b.

Unlike cam member 410, a cam member 510 includes two slanted or angled cam slots 510a and 510b that are configured to house respective stationary cam pins 511a and 511b that are operably coupled to the jaw members 120 and 110, respectively. Cam member 510 is movable along the longitudinal axis "A-A." In certain embodiments, the cam slots 510a and 510b may be in the jaw members 110 and 120 and the cam pins 511a and 511b may be attached to the cam member 510.

In use, proximal movement of the movable handle 40 causes the driving structure 133 including the bifurcated distal end 135 to move distally, thus, moving the cam member 510 including the cam slots 510a and 510b distally, which, in turn, cams the cam pins 511a and 511b causing the jaw members 110 and 120 to move toward each other to the clamping position (FIG. 7). Distal motion of movable handle 40 causes the driving structure 133 including the bifurcated distal end 135 to move proximally, thus, moving the cam member 510 including the cam slots 510a and 510b proximally, which, in turn, cams the cam pins 511a and 511b causing the jaw members 110 and 120 to move away from each other to the open position.

Figure 8:
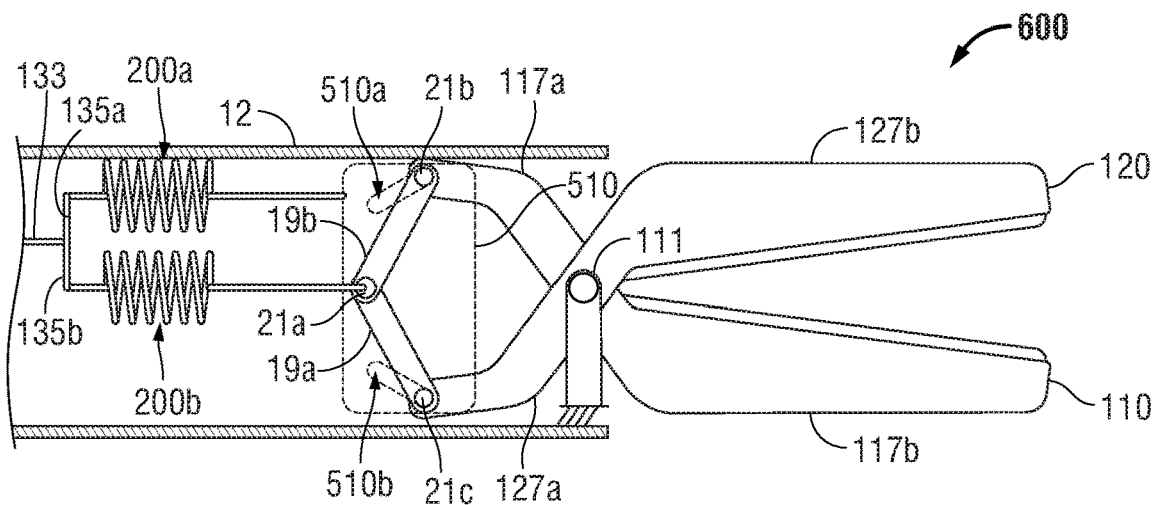
FIG. 8 is a schematic view illustrating an end effector assembly including jaw members according to still yet another embodiment of the present disclosure.

With reference to FIG. 8, an end effector assembly 600 is illustrated. End effector assembly 600 is substantially similar to end effector 500. As a result thereof, only those features unique to end effector 600 are described herein.

Unlike the previously described jaw members, the jaw members 110 and 120 illustrated in FIG. 8 include respective proximal ends 117a and 127a that are "offset" from the respective distal ends 117b and 127b.

In the embodiment illustrated in FIG. 8, the cam pin 21b operably couples the link 19b, the cam slot 510a and the proximal end 117a of the jaw member 110 to each other. Likewise, the cam pin 21c operably couples the link 19a, the cam slot 510b and the proximal end 127a of the jaw member 120 to each other.

In use, proximal movement of the movable handle 40 causes the driving structure 133 including the bifurcated distal end 135 to move distally, thus, moving the cam member 510 including the cam slots 510a and 510b distally, which, in turn, cams the cam pins 511a and 511b causing the jaw members 110 and 120 to move away from each other to the open position (FIG. 8). Distal motion of movable handle 40 causes the driving structure 133 including the bifurcated distal end 135 to move proximally, thus, moving the cam member 510 including the cam slots 510a and 510b proximally, which, in turn, cams the cam pins 511a and 511b causing the jaw members 110 and 120 to toward each other to the closed position.

Figure 9:
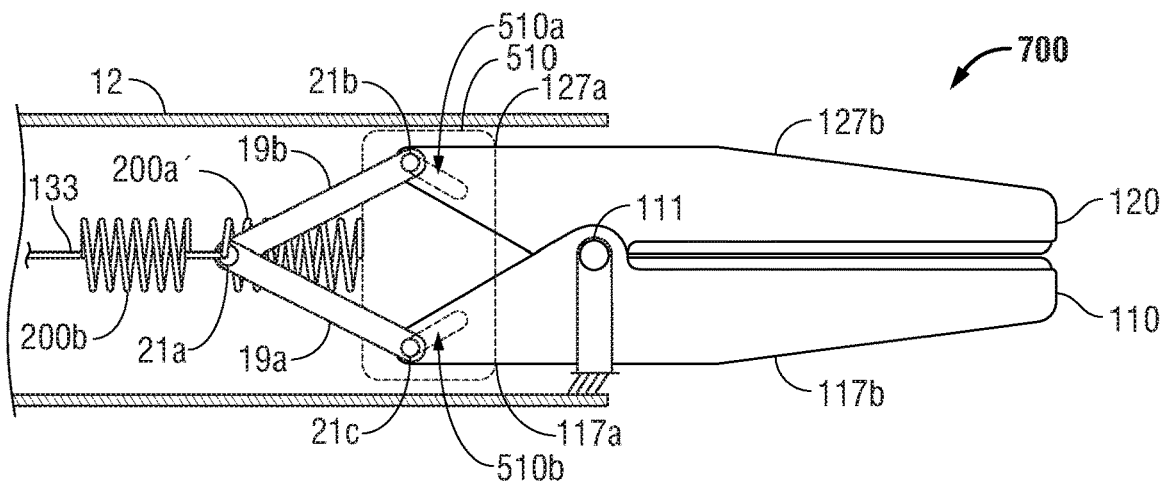
FIG. 9 is a schematic view illustrating an end effector assembly including jaw members according to yet another embodiment of the present disclosure.

With reference to FIG. 9, an end effector assembly 700 is illustrated. End effector assembly 700 is substantially similar to end effector 600. As a result thereof, only those features unique to end effector 700 are described herein.

In the embodiment illustrated in FIG. 9, the cam pin 21b operably couples the link 19b, the cam slot 510a and the proximal end 127a of the jaw member 120 to each other. Likewise, the cam pin 21c operably couples the link 19a, the cam slot 510b and the proximal end 117a of the jaw member 110 to each other.

The driving structure 133 does not include a bifurcated distal end 135. Accordingly, unlike the resilient member 200a that includes a proximal end that operably couples to the branch 135a of the driving structure 133, a proximal end of the resilient member 200a' is operably coupled to the pivot pin 21a (FIG. 9). Moreover, the spring 200a' is disposed in the same horizontal plane as the spring 200b.

In use, proximal movement of the movable handle 40 causes the driving structure 133 to move distally, thus, moving the cam member 510 including the cam slots 510a and 510b distally, which, in turn, cams the pivot pins 21b and 21c causing the jaw members 110 and 120 to move toward each other to the clamping position (FIG. 9). Distal motion of movable handle 40 causes the driving structure 133 to move proximally, thus, moving the cam member 510 including the cam slots 510a and 510b proximally, which, in turn, cams the pivot pins 21b and 21c causing the jaw members 110 and 120 to move away from each other to the open position.

Figure 10:
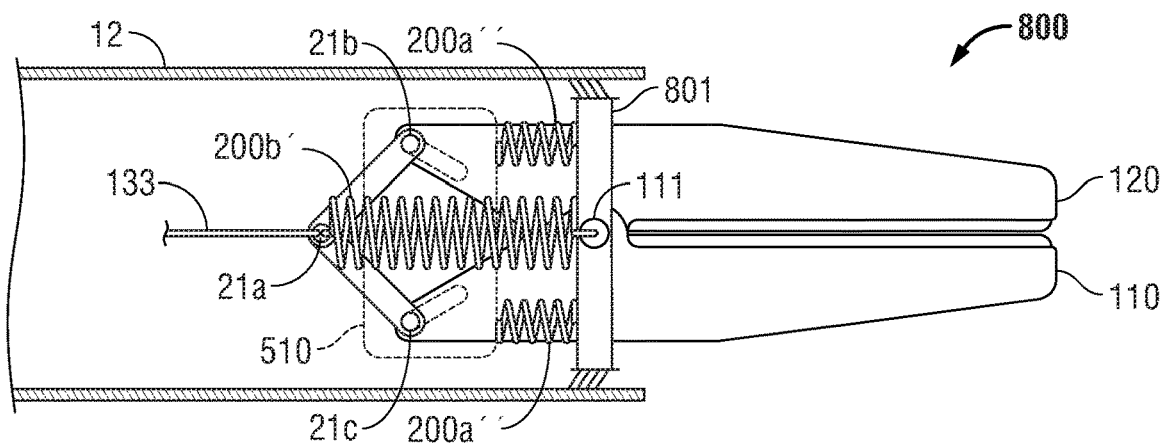
FIG. 10 is a schematic view illustrating an end effector assembly including jaw members according to still yet another embodiment of the present disclosure.

With reference to FIG. 10, an end effector assembly 800 is illustrated. End effector assembly 800 is substantially similar to end effector 700. As a result thereof, only those features unique to end effector 800 are described herein.

A support structure 801 of suitable proportion is operably disposed adjacent the end effector 800. Support structure 801 is configured to couple to one or more resilient members 200a".

In the embodiment illustrated in FIG. 10 two resilient members 200a" are illustrated. Each resilient member 200a" includes proximal ends that couple to a distal end of the cam member 510 and distal ends that operably couple to the support structure 801.

A third resilient member 200b' includes a proximal end that operably couples to the pivot pin 21a and a distal end that operably couples to the support structure 801.

In use, proximal movement of the movable handle 40 causes the driving structure 133 to move distally, thus, moving the cam member 510 including the cam slots 510a and 510b distally, which, in turn, cams the pivot pins 21b and 21c causing the jaw members 110 and 120 to move toward each other to the clamping position (FIG. 10). Distal motion of movable handle 40 causes the driving structure 133 to move proximally, thus, moving the cam member 510 including the cam slots 510a and 510b proximally, which, in turn, cams the pivot pins 21b and 21c causing the jaw members 110 and 120 to move away from each other to the open position.

Figure 11:
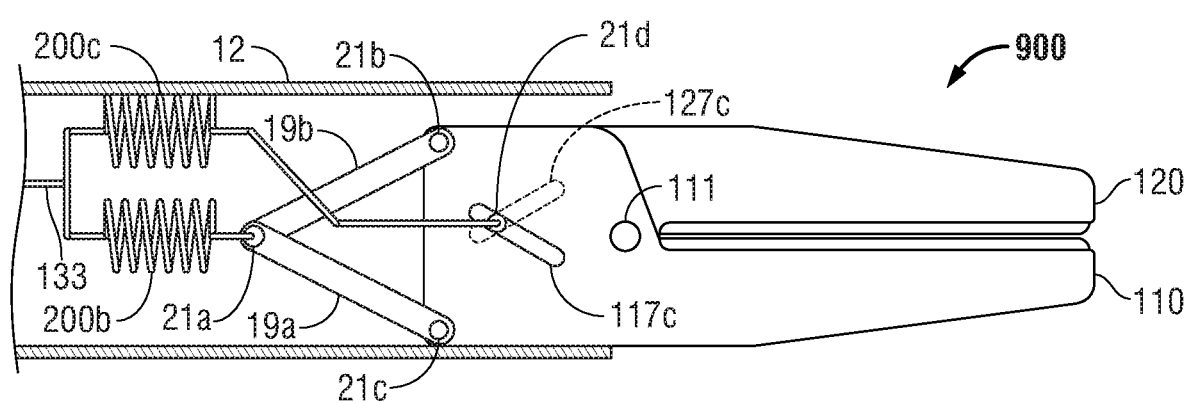
FIG. 11 is a schematic view illustrating an end effector assembly including jaw members according to yet another embodiment of the present disclosure.

With reference to FIG. 11, an end effector assembly 900 is illustrated. End effector assembly 900 is substantially similar to end effectors 500 and 600. As a result thereof, only those features unique to end effector 900 are described herein.

A resilient member 200c includes a distal end that operably couples to a cam pin 21d that is operably coupled to a pair of cam slots 127c and 117c that are disposed on respective jaw members 120 and 110 at proximal ends 127a and 117a thereof.

In use, proximal movement of the movable handle 40 causes the driving structure 133 including bifurcated distal end 135 to move proximally, thus, moving the cam pin 21d proximally within the cam slots 127c and 117c, which, in turn, causes the jaw members 110 and 120 to move toward each other to the clamping position (FIG. 11). Distal motion of movable handle 40 causes the driving structure 133 including the bifurcated distal end 135 to move distally, thus, moving the cam pin 21d distally within the including the cam slots 127c and 117c, which, in turn, causes the jaw members 110 and 120 to move away from each other to the open position.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a shaft;
    an end effector assembly disposed at a distal end portion of the shaft, the end effector assembly including first and second jaw members pivotably coupled to the shaft about a pivot such that at least one of the first or second jaw members is movable relative to the shaft and the other of the first or second jaw members between an open position, wherein the first and second jaw members are disposed in spaced relation relative to one another, and a closed position, wherein the first and second jaw members cooperate to grasp tissue therebetween;
    a driving structure disposed within the shaft and configured for translation relative to the shaft;
    a linkage assembly operably coupled between the driving structure and the first and second jaw members such that translation of the driving structure relative to the shaft moves the at least one of the first or second jaw members between the open position and the closed position, the linkage assembly defining a leading edge;
    at least one stop member positioned in the shaft, the at least one stop member configured to contact the leading edge of the linkage assembly to releasably lock the at least one of the first or second jaw members in the closed position; and
    a spring disposed between the pivot and the driving structure, the spring configured to bias the at least one of the first or second jaw members.

2. The surgical instrument according to claim 1, wherein the spring is configured to bias the at least one of the first or second jaw members towards the open position.

3. The surgical instrument according to claim 1, wherein the spring is configured to bias the at least one of the first or second jaw members towards the closed position to provide a closure force between the first and second jaw members.

4. The surgical instrument according to claim 3, wherein the closure force is in a range of about 3 kg/cm$^2$ to about 16 kg/cm$^2$.

5. The surgical instrument according to claim 1, wherein each of the first and second jaw members is pivotable relative to the shaft and the other of the first and second jaw members between the open and closed positions.

6. The surgical instrument according to claim 1, wherein the driving structure includes at least one of: a rod, a cable, a wire, or a band.

7. The surgical instrument according to claim 1, wherein the spring includes a proximal end fixed relative to the shaft and a distal end movable relative to the shaft.

8. The surgical instrument according to claim 1, wherein the spring includes a distal end fixed relative to the shaft and a proximal end movable relative to the shaft.

9. The surgical instrument according to claim 1, further comprising a housing, wherein the shaft extends distally from the housing.

10. The surgical instrument according to claim 9, further comprising a movable handle operably associated with the driving structure, the movable handle movable relative to the housing to translate the driving structure relative to the shaft.

11. The surgical instrument according to claim 1, wherein the linkage assembly includes first and second links.

12. The surgical instrument according to claim 11, wherein the first link is operably coupled between the driving structure and the first jaw member, and wherein the second link is operably coupled between the driving structure and the second jaw member.

13. The surgical instrument according to claim 12, wherein the first and second links are operably coupled to one another and the driving structure at proximal end portions of the first and second links.

14. The surgical instrument according to claim 1, wherein the linkage assembly is disposed proximally of the spring.

15. The surgical instrument according to claim 1, wherein each of the first and second jaw members includes an opposed electrically conductive tissue contacting surface.

* * * * *